(12) United States Patent
Liu

(10) Patent No.: US 9,693,586 B2
(45) Date of Patent: Jul. 4, 2017

(54) ANTI-TAMPER ATOMIZER AND ELECTRONIC CIGARETTE

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 1085 days.

(21) Appl. No.: 13/895,726

(22) Filed: May 16, 2013

(65) Prior Publication Data

US 2014/0283857 A1 Sep. 25, 2014

Related U.S. Application Data

(63) Continuation of application No. PCT/CN2013/073015, filed on Mar. 21, 2013.

(51) Int. Cl.
*A24F 47/00* (2006.01)
*A61M 15/06* (2006.01)

(52) U.S. Cl.
CPC ........... *A24F 47/008* (2013.01); *A61M 15/06* (2013.01); *A61M 2205/273* (2013.01)

(58) Field of Classification Search
CPC .............................. A24F 47/00; A24F 47/008
See application file for complete search history.

(56) References Cited

FOREIGN PATENT DOCUMENTS

| CN | 1270130 A | 10/2000 |
|---|---|---|
| CN | 101606758 A | 12/2009 |
| CN | 201869778 U | 6/2011 |
| CN | 202233005 U | 5/2012 |
| WO | 2008130813 A1 | 10/2008 |
| WO | 2011124033 A1 | 10/2011 |

OTHER PUBLICATIONS

English Mechanical Translation of CN 202233005, Original Patent published on May 30, 2012, printed from http://translationportal.epo.org/emtp/translate/?ACTION=description-retrieval&COUNTRY=CN&ENGINE=google&FORMAT=docdb&KIND=U&LOCALE=en__EP&NUMBER=202233005&OPS=ops.epo.org/3.1&SRCLANG=zh&TRGLANG=en.*
International Search Report mailed Jan. 2, 2014 in International Application No. PCT/CN2013/073015 filed Mar. 21, 2013.

* cited by examiner

*Primary Examiner* — Michael H Wilson
*Assistant Examiner* — Dionne Walls Mayes
(74) *Attorney, Agent, or Firm* — Tim Tingkang Xia, Esq.; Locke Lord LLP

(57) ABSTRACT

The present invention relates to an anti-tamper atomizer and electronic cigarette. Wherein the anti-tamper atomizer comprises a protective sleeve, a suction nozzle cap fixed on a first end of the protective sleeve, and a battery cartridge connector fixed on a second end of the protective sleeve; a vent pipe, a heater strip component and an oil storage cotton coated outside of the vent pipe and the heater strip component are arranged in the protective sleeve, the battery cartridge connector comprises a protective sleeve connecting part and a battery cartridge connecting part connected with each other, wherein the battery cartridge connector has a center hole extending along the axis of the protective sleeve, and a groove is formed at the adjacency of the protective sleeve connecting part and the battery cartridge connecting part.

4 Claims, 7 Drawing Sheets

ANTI-TAMPER ATOMIZER AND ELECTRONIC CIGARETTE

CROSS-REFERENCE TO RELATED APPLICATIONS

This application is a continuation of International Patent Application No. PCT/CN2013/073015, with an international filing date of Mar. 21, 2013, designating the United States, now pending. The contents of these specifications are incorporated herein by reference.

FIELD OF THE INVENTION

The present invention relates to a daily electronic product, and more particularly to an anti-tamper atomizer and electronic cigarette.

BACKGROUND OF THE INVENTION

The traditional cigarette is replaced by the electronic cigarette gradually as the health consciousness increases. A one-off electronic cigarette in the prior art comprises an atomizer and a battery cartridge connected with each other. FIG. 1 is a schematic diagram showing the atomizer 100 of the one-off electronic cigarette in the prior art. As shown in FIG. 1, the atomizer 100 comprises a protective sleeve 101, and an oil storage cotton 102 and a heater strip component 103 which are arranged in the protective sleeve, wherein a battery and a controller (not shown in the figure) are arranged in the protective sleeve, and the heater strip component 103 is electrically connected with the battery. A suction nozzle cap 104 is arranged on a first end of the atomizer 100, and the heater strip component 103 is electrified and emits heat when the smoker smokes, so as to atomize the cigarette liquid in the oil storage cotton 102 and form smoke for inhaling by the human body.

A connector 105 is arranged on a second end of the atomizer 100, the lower of the connector 105 is fixed in the protective sleeve 101, and the upper of the connector 105 extends out form the protective sleeve 101 and connects with the battery cartridge by male screw. When the one-off electronic cigarette is used up, the atomizer 100 is loosened off from the battery cartridge and is replaced by a new atomizer 100 so that the one-off electronic cigarette can be reused.

The defect of this atomizer is that, when an force is applied on the connector 105 at the direction perpendicular to the protective sleeve 101 to bend the connector, the connector 105 can be loosened off from the protective sleeve 101 easily, the oil storage cotton 102 can be taken out and the unqualified cigarette oil which contains a lot of harmful substance and will damage the health of the smoker can be add into the oil storage cotton 102 for reuse.

SUMMARY OF THE INVENTION

Aiming at the defects of being loosened off easily of the atomizer in the prior art, the technical problem to be solved by the present invention is to provide an anti-tamper atomizer and electronic cigarette so as to prevent the atomizer from being loosened off.

The present invention adopts the following technical solution to solve its technical problem: an anti-tamper atomizer, comprising a protective sleeve, a suction nozzle cap fixed on a first end of the protective sleeve, and a battery cartridge connector fixed on a second end of the protective sleeve, a vent pipe, a heater strip component and an oil storage cotton coated outside of the vent pipe and the heater strip component are arranged in the protective sleeve, the battery cartridge connector comprises a protective sleeve connecting part and a battery cartridge connecting part connected with each other, wherein the battery cartridge connector has a center hole extending along the axis of the protective sleeve, and a groove is formed at the adjacency of the protective sleeve connecting part and the battery cartridge connecting part.

The anti-tamper atomizer according to the present invention, wherein the battery cartridge connector has a wall thickness of 0.05-0.2 mm at the groove.

The anti-tamper atomizer according to the present invention, wherein the protective sleeve is in cylindric shape, and the peripheral of the cross section of battery cartridge connector at the direction perpendicular to the axis of the protective sleeve is in shape of any one of quadrate, circular, triangular, cone, trapeziform, and undee shape.

The anti-tamper atomizer according to the present invention, wherein the peripheral surface of the cross section of battery cartridge connector at the groove in the direction perpendicular to the axis of the protective sleeve comprises multiple recesses arranged alternately, and a bulge is formed between every two adjacent recesses.

The anti-tamper atomizer according to the present invention, wherein the battery cartridge connector has a wall thickness of 0.05-0.1 mm at the recess and a wall thickness of 0.1-0.2 mm at the bulge.

The anti-tamper atomizer according to the present invention, wherein the protective sleeve connecting part is fixed in the protective sleeve by interference fit.

The anti-tamper atomizer according to the present invention, wherein a chamfer for assisting inserting into the protective sleeve is formed on one end of protective sleeve connecting part which far away form the battery cartridge connecting part.

The anti-tamper atomizer according to the present invention, wherein a male screw is formed on the battery cartridge connecting part.

The anti-tamper atomizer according to the present invention, further comprises a first insulating ring fixed in the battery cartridge connector and a first electrode fixed in the first insulating ring, wherein the first insulating ring is made of elastic material; a first retaining groove is formed on the peripheral surface of the first insulating ring, a first protrudent ring extending along the radial direction of the protective sleeve is formed in the protective sleeve connecting part, and the first retaining groove is engaged with the first protrudent ring.

The anti-tamper atomizer according to the present invention, wherein the suction nozzle cap comprises a cover plate with a center hole, an outer cylinder wall extending perpendicularly from the cover plate and fixed in the first end of the of the protective sleeve by interference fit, and an inner cylinder wall extending perpendicularly from the periphery of the center hole on the cover plate.

The anti-tamper atomizer according to the present invention, wherein oil storage cotton is in cylindric shape, with one end supported on the end of the outer cylinder wall of the suction nozzle cap and another end sleeved by the protective sleeve connecting part of the battery cartridge connector.

An electronic cigarette is provided and comprises a battery cartridge and the anti-tamper atomizer described above, wherein the battery cartridge and the anti-tamper atomizer connect with each other.

When implementing the anti-tamper atomizer and electronic cigarette of the present invention, the following advantageous effect can be achieved: the groove is formed on the battery cartridge connector, so that the wall at the groove is very thin and the battery cartridge connector will be broken at the groove when a force is a applied on the battery cartridge connector at the direction perpendicular to the protective sleeve to bend the battery cartridge connector, the battery cartridge connector will not be loosened off, the anti-tamper object is achieved, the unqualified cigarette oil can be prevented from being add into the oil storage cotton of the one-off electronic cigarette and reuse is avoided.

BRIEF DESCRIPTION OF THE DRAWINGS

The present invention will be described in detail with reference to the accompanying drawings and embodiments, in the accompanying drawings.

DETAILED DESCRIPTION OF THE EMBODIMENT

The objective, technical scheme and advantages of the present invention will be more apparent from the following detailed description of the present invention with reference to the accompanying drawings and embodiments. It should be understand that the embodiment is described herein to illustrate the present invention, and is not limitation.

Figure 1:
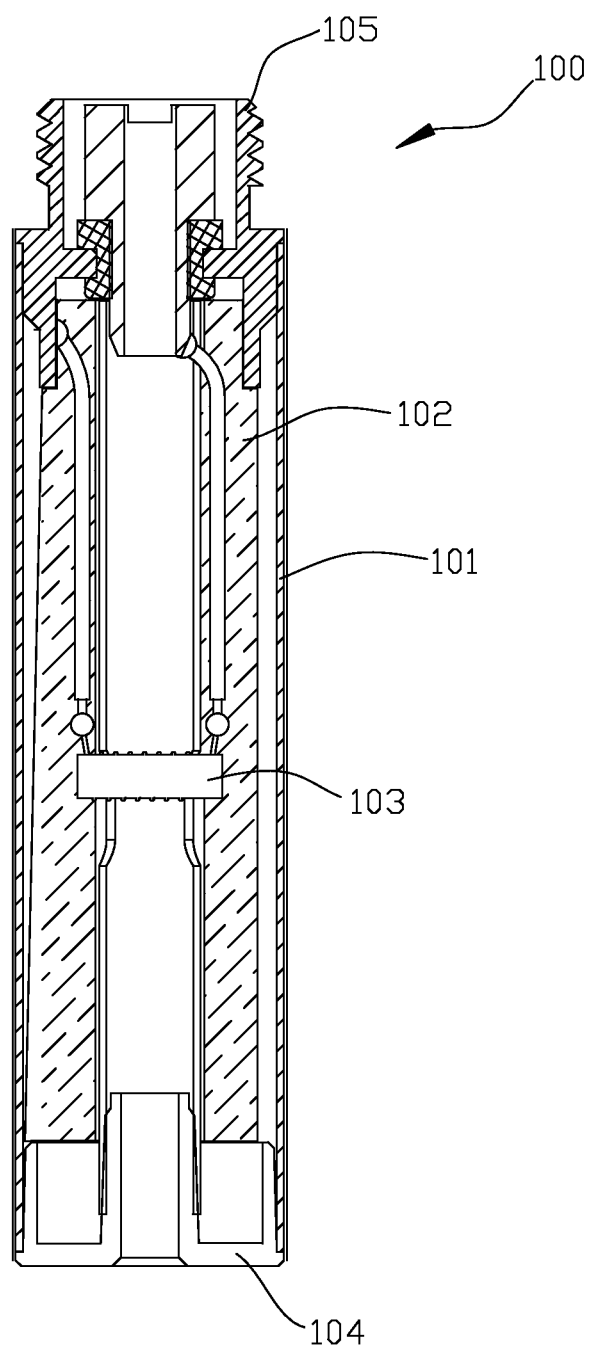
FIG. 1 is a schematic diagram showing a atomizer 100 of a one-off electronic cigarette in the prior art.
Figure 2:
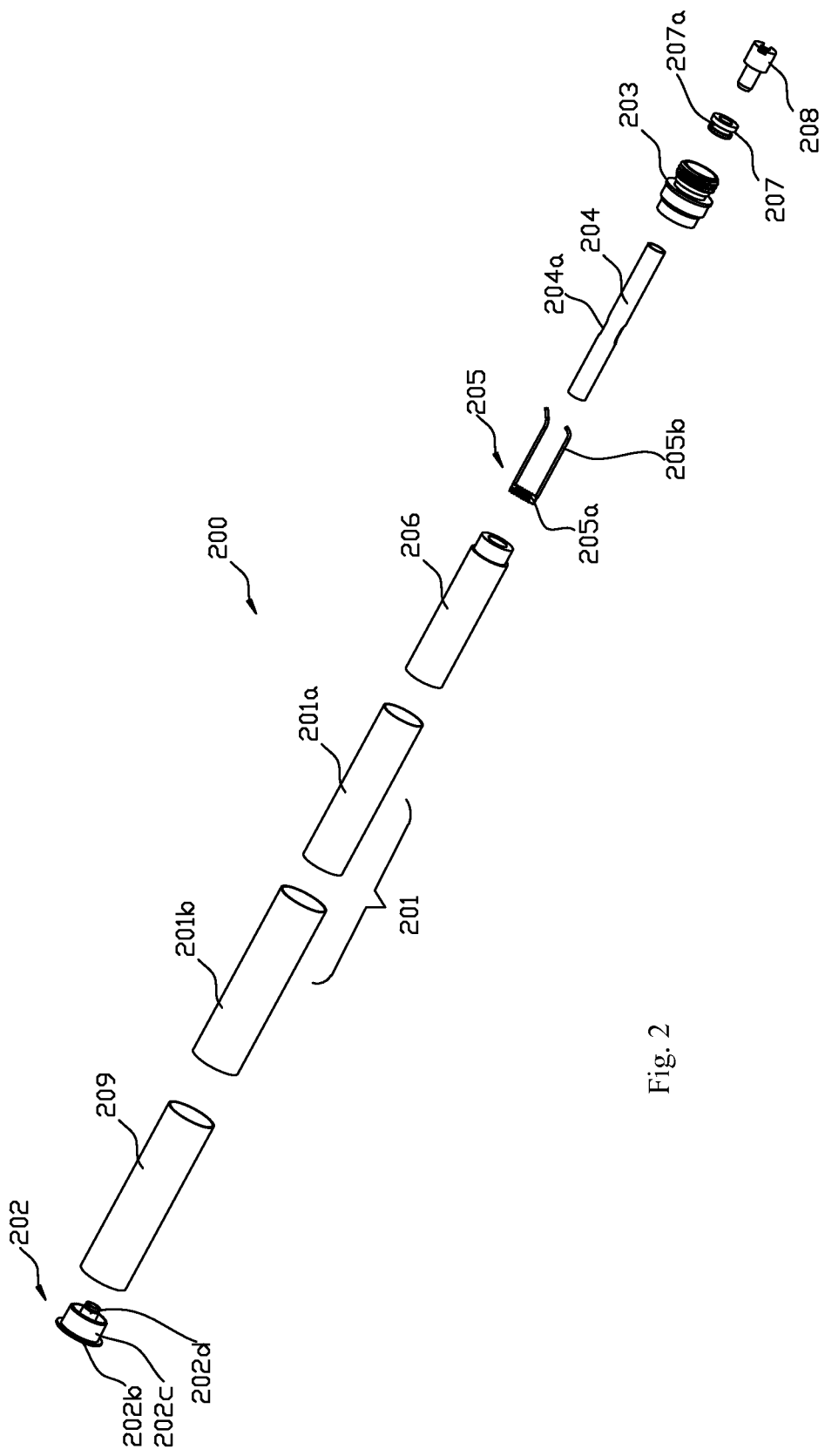
FIG. 2 is a schematic explosive view showing the atomizer according to the present invention.
Figure 3:
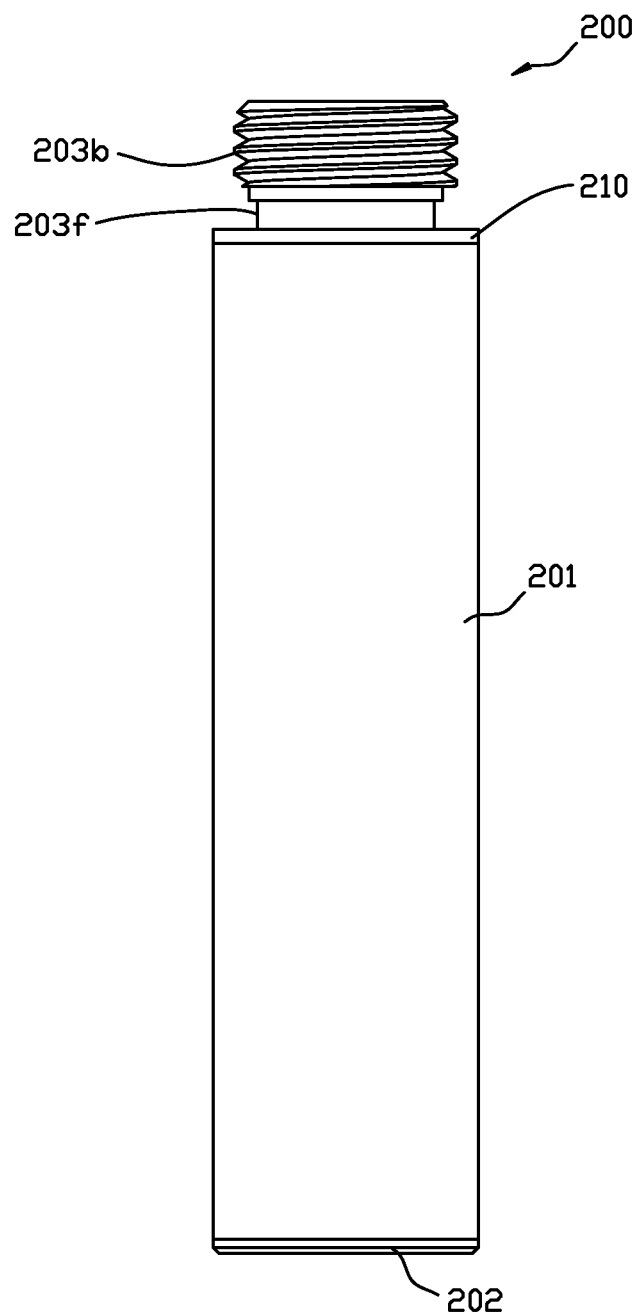
FIG. 3 is a schematic diagram showing the atomizer according to the present invention.
Figure 4:
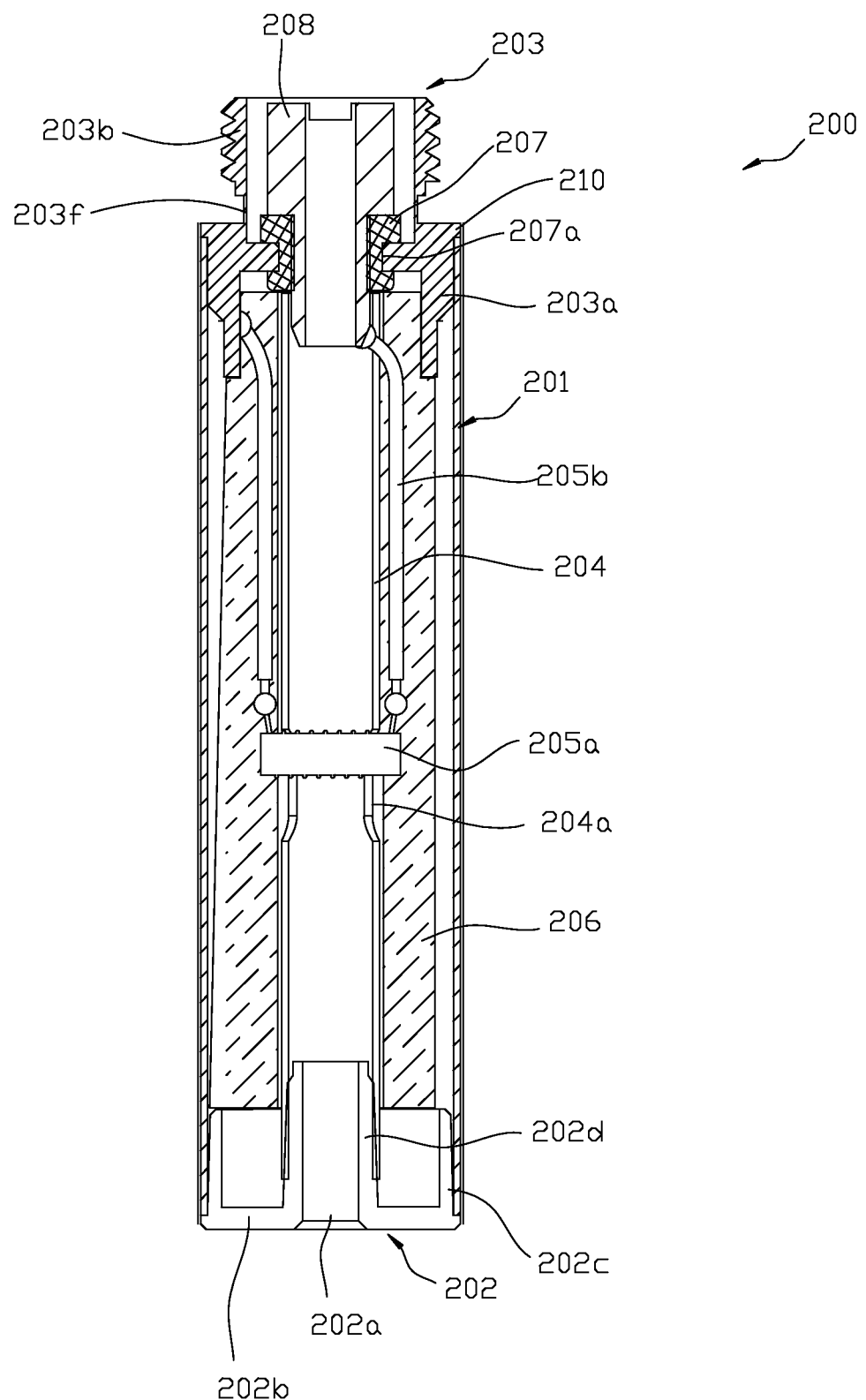
FIG. 4 is a cutaway view showing the atomizer in FIG. 3.

A one-off electronic cigarette in the present invention comprises an atomizer 200 and a battery cartridge 300 connected with each other. FIG. 2 is a schematic explosive view showing the atomizer 200 according to the present invention; FIG. 3 is a schematic diagram showing the atomizer 200 according to the present invention; and FIG. 4 is a cutaway view showing the atomizer 200 in FIG. 3. As shown in FIGS. 2-4, the atomizer 200 comprises a protective sleeve 201, a suction nozzle cap 202 fixed on a first end of the protective sleeve 201, and a battery cartridge connector 203 fixed on a second end of the protective sleeve 201. The protective sleeve 201 is in cylindric shape. A vent pipe 204 is arranged in the protective sleeve 201, a heater strip component 205 is arranged on the vent pipe 204 immovably, and an oil storage cotton 206 coats the heater strip component 205 and the vent pipe 204.

The suction nozzle cap 202 comprises a cover plate 202b with a center hole 202a, and an outer cylinder wall 202c extending perpendicularly from the cover plate 202b, and an inner cylinder wall 202d extending perpendicularly from the periphery of the center hole 202a, wherein the outer cylinder wall 202c and the inner cylinder wall 202d extends at the same direction. The outer cylinder wall 202c is fixed in the first end of the of the protective sleeve 201 by interference fit.

Figure 6:
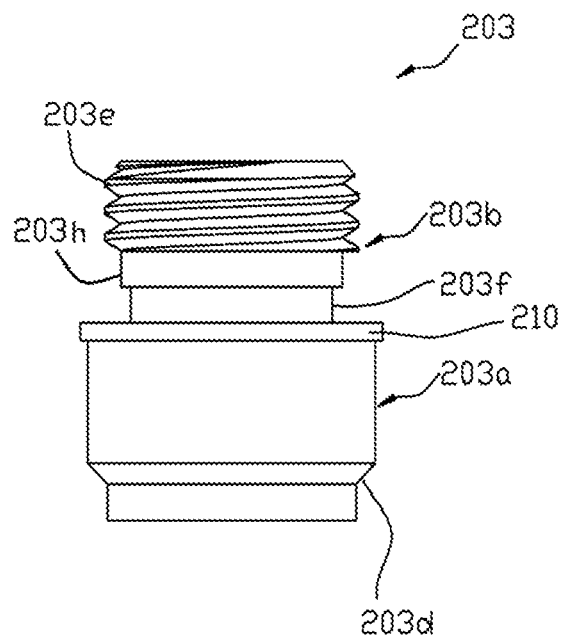
FIG. 6 is a schematic diagram showing a battery cartridge connector according to the present invention.
Figure 7:
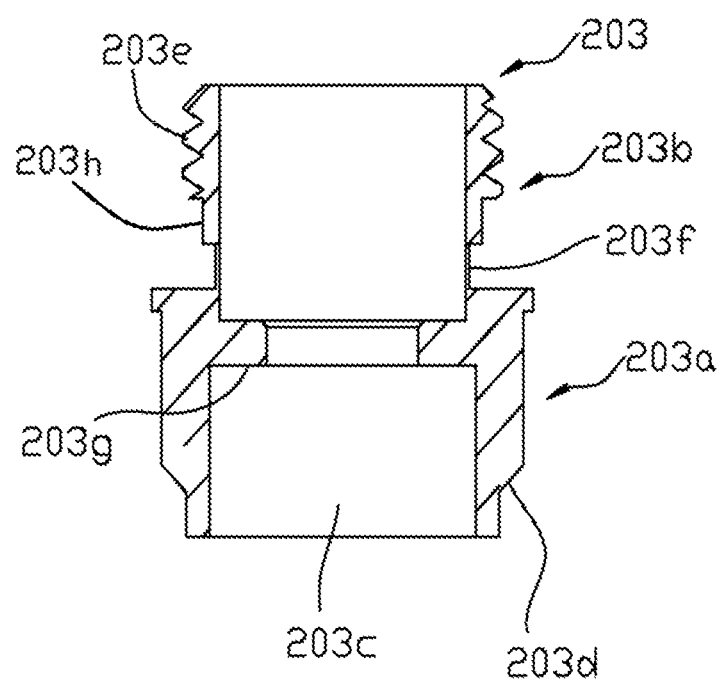
FIG. 7 is a cutaway view showing the battery cartridge connector according to the present invention.

FIG. 6 is a schematic diagram showing a battery cartridge connector according to the present invention; FIG. 7 is a cutaway view showing the battery cartridge connector according to the present invention. As shown in FIG. 6 and FIG. 7, the battery cartridge connector 203 comprises a protective sleeve connecting part 203a and a battery cartridge connecting part 203b connected with each other. The battery cartridge connector 203 has a center hole 203c extending along the axis of the protective sleeve 201. The protective sleeve connecting part 203a is fixed in the second end of the protective sleeve 201 by interference fit, and a chamfer 203d is formed on one end of protective sleeve connecting part 203a which far away from the battery cartridge connecting part 203b, so as to assist inserting into the protective sleeve 201. The battery cartridge connecting part 203b is exposed out of the protective sleeve 201. A male screw 203e for connecting the battery cartridge is formed on the battery cartridge connecting part 203b.

A groove 203f is formed at the adjacency of the protective sleeve connecting part 203a and the battery cartridge connecting part 203b, so that the battery cartridge connector 203 will not be loosen off easily after being fixed to the protective sleeve 201. The groove 203f is formed by cutting the outer surface 203h of the battery cartridge connector 203, and the peripheral of the cross section of battery cartridge connector 203 at the groove 203f in the direction perpendicular to the axis of the protective sleeve 201 is in shape of any one of quadrate, circular, triangular, cone, trapeziform, and undee shape.

Figure 8:
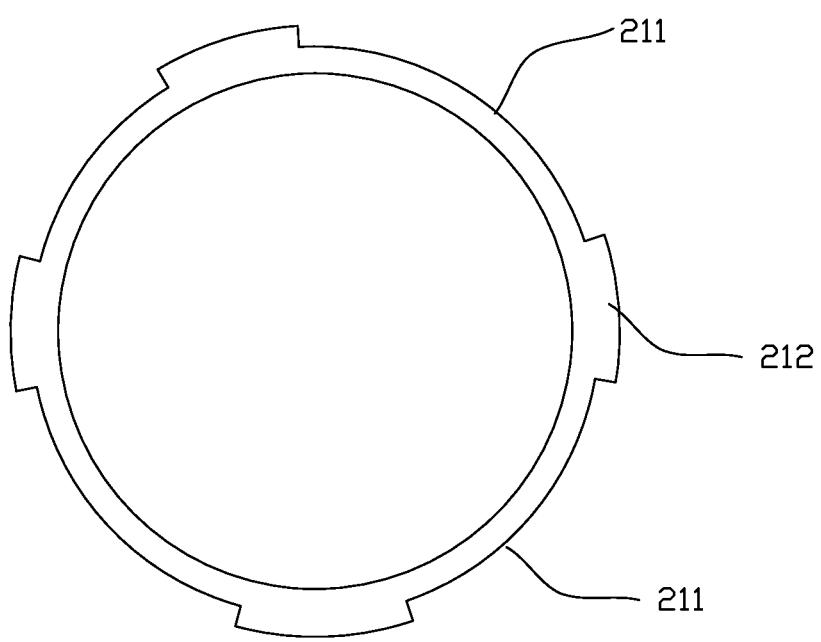
FIG. 8 is a cross section view of the battery cartridge connector along a groove.

As shown in FIG. 8, the peripheral of the cross section of battery cartridge connector 203 at the groove 203f in the direction perpendicular to the axis of the protective sleeve 201 may be other un-regular shape, for example, comprising multiple recesses 211 arranged alternately, these recesses 211 are positioned uniformly or un-uniformly on a same circumference around the axis of the protective sleeve 201. A bulge 212 is formed between every two adjacent recesses 211, and the depths of the recesses 211 may be the same or different from each other; similarly, the heights of the bulges 212 may be the same or different from each other.

The depth of the groove 203f is configured that the battery cartridge connector 203 has a wall thickness of 0.05-0.2 mm at the groove 203f. The wall is very thin, so that the battery cartridge connector 203 will be broken at the groove 203f when a force is a applied on the battery cartridge connector 203 at the direction perpendicular to the protective sleeve 201 to bend the battery cartridge connector 203, the battery cartridge connector 203 will not be loosened off, and the anti-tamper object is achieved. If the thickness of the wall at the groove 203f is less than 0.05 mm, the battery cartridge connector 203 will be difficult to produce and the strength of the battery cartridge connector 203 will be not sufficient; and If the thickness of the wall at the groove 203f is more than 0.2 mm, it will be difficult to break the battery cartridge connector 203 when a force is applied to bend it.

In the embodiment as shown in FIG. 8, the battery cartridge connector 203 has a wall thickness of 0.05-0.1 mm at the recess 211 and a wall thickness of 0.1-0.2 mm at the bulge 212.

A flange 210 is formed on the out surface of the protective sleeve connecting part 203a, and the flange 210 is formed on one end of the protective sleeve connecting part 203a closed to the groove 203f. When the protective sleeve connecting part 203a is fixed in the second end of the protective sleeve 201, the flange 210 presses against the end surface on the second end of the protective sleeve 201 so as to limit the position of the battery cartridge connector 203 and facilitate the assembling.

A first protrudent ring 203g extending along the radial direction of the protective sleeve 201 is formed in the protective sleeve connecting part 203a. A first insulating ring 207 is fixed in the battery cartridge connector 203. The first insulating ring 207 is in shape of circular ring and a first retaining groove 207a is formed on its peripheral surface. The whole first insulating ring 207 is made of elastic material, and the first retaining groove 207a is engaged with the first protrudent ring 203g so as to fix the first insulating ring 207 into the battery cartridge connector 203. A first electrode 208 is fixed in the first insulating ring 207 by interference fit. The first electrode 208 is electrically connected with the heater strip component 205.

As shown in FIGS. 2-4, one end of the vent pipe 204 sleeves outside the inner cylinder wall 202d of the suction nozzle cap 202, and the other end presses against the first insulating ring 207 so that the vent pipe 204 is retained in position.

Two opposite vent holes 204a are formed on the vent pipe 204 and go through its peripheral wall. The heater strip component 205 is arranged on the vent pipe 204 immovably. The heater strip component 205 comprises a heater strip body 205a and extending legs 205b extending from two ends of the heater strip body 205a, the heater strip body 205a passes through the two vent holes 204a and the extending legs 205b clamp on the out surface of the vent pipe 204 so that the heater strip component 205 is fixed.

The oil storage cotton 206 is in cylindric shape substantially and sleeves the heater strip component 205 and the vent pipe 204. One end of the oil storage cotton 206 is supported on the end of the outer cylinder wall 202c of the suction nozzle cap 202 and another end is sleeved by the protective sleeve connecting part 203a of the battery cartridge connector 203 such that the oil storage cotton 206 is fixed. A gap is formed between the protective sleeve 201 and the oil storage cotton 206.

The protective sleeve 201 may comprises an inner protective sleeve 201a and an outer protective sleeve 201b, wherein the inner protective sleeve 201a is made of material such as metal, china, etc.; the outer protective sleeve 201b is sleeved on the outer protective sleeve 201b and is made of material such as metal, plastic, wood, paper, etc. A paster 209 may be arranged on the out surface of the protective sleeve 201.

Figure 5:
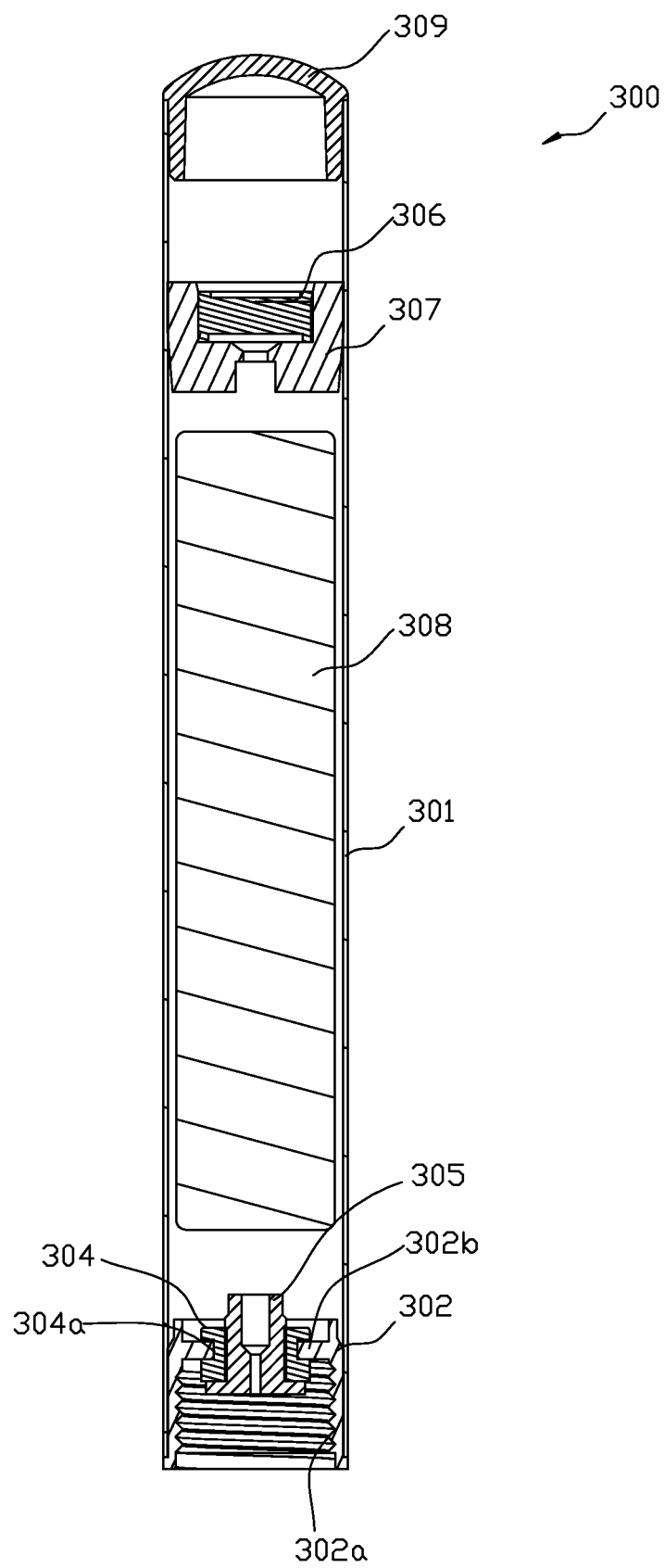
FIG. 5 is a cutaway view showing a battery cartridge according to the present invention.

FIG. 5 is a cutaway view showing a battery cartridge 300 according to the present invention. As shown in FIG. 5, the battery cartridge 300 comprises a cylindric battery sleeve 301, and a atomizer connector 302 is arranged in a first end of the battery sleeve 301, wherein the atomizer connector 302 is in cylindric shape substantially and is fixed in the battery sleeve 301 by means such as interference fit, screw, etc. A female screw 302a for engaging with the male screw 203e on the battery cartridge connector 203 is formed in the atomizer connector 302, so as to connect the atomizer 200 and the battery cartridge 300.

A second protrudent ring 302b extending along the radial direction of the battery sleeve 301 is formed in the atomizer connector 302. A second insulating ring 304 is fixed in the atomizer connector 302. The second insulating ring 304 is in cylindric shape, and a second retaining groove 304a is formed on the peripheral surface of the second insulating ring 304. The whole second insulating ring 304 is made of elastic material, and the second retaining groove 304a on the second insulating ring 304 engages with the second protrudent ring 302b so as to fix the second insulating ring 304 into the atomizer connector 302. A second electrode 305 is fixed in the second insulating ring 305 by interference fit. The first electrode 208 is electrically connected with the second electrode 305 when the atomizer 200 and the battery cartridge 300 are connected with each other.

A controller 306 and a controller seat 307 for supporting the controller 306 are arranged in the battery sleeve 301. A battery 308 is arranged between the controller seat 307 and the atomizer connector 302 and is electrically connected with the controller 306 and the second electrode 305 via electrical wires. A light cap 309 is fixed in the second end of the battery sleeve 301.

When the smoker smokes via the suction nozzle cap 202 during use, the controller 306 senses the change of the airflow, connects the battery 308 and the second electrode 305, and further transfers the current flow to the heater strip component 205 via the first electrode 208 so as to atomize the cigarette liquid in the oil storage cotton 206 and form much smoke for inhaling by the human body.

The atomizer 200 can be loosened off and replaced by a new atomizer 200 when the one-off electronic cigarette is used up. The groove 203f is formed on the battery cartridge connector 203 of the atomizer 200, so that the wall at the groove 203f is very thin and the battery cartridge connector 203 will be broken at the groove 203f when a force is a applied on the battery cartridge connector 201 at the direction perpendicular to the protective sleeve 201 to bend the battery cartridge connector 203, the battery cartridge connector 203 will not be loosened off, the anti-tamper object is achieved, the unqualified cigarette oil can be prevented from being add into the atomizer 200 of the one-off electronic cigarette and reuse is avoided.

While the preferred embodiments are described above, but they are not limitation. Any modification, equivalent substitution, and improvement within the spirit and principle should be included in the protecting scope of the present invention.

What is claimed is:

1. An anti-tamper atomizer, comprising a protective sleeve, a suction nozzle cap fixed on a first end of the protective sleeve, and a battery cartridge connector fixed on a second end of the protective sleeve, a vent pipe, a heater strip component and an oil storage cotton coated outside of the vent pipe and the heater strip component are arranged in the protective sleeve, the battery cartridge connector comprises a protective sleeve connecting part and a battery cartridge connecting part connected with each other, wherein the battery cartridge connector has a center hole extending along the axis of the protective sleeve, and a groove formed by cutting an outer surface of the battery cartridge connector is formed at an adjacency of the protective sleeve connecting part and the battery cartridge connecting part;

wherein a peripheral surface of a cross section of battery cartridge connector at the groove in a direction perpendicular to an axis of the protective sleeve comprises multiple recesses arranged alternately, and a bulge is formed between every two adjacent recesses;

wherein the recesses are positioned uniformly on a same circumference around the axis of the protective sleeve; depths of the recesses are the same, and height of each bulge is same with each other;

wherein the battery cartridge connector has a wall thickness of 0.05 mm to 0.1 mm at the recesses and a wall thickness of 0.1 mm to 0.2 mm at the bulge; and wherein the battery cartridge connector groove is broken at the groove when a force is applied on the battery cartridge connector at a direction perpendicular to the protective sleeve to bend the battery cartridge connector.

2. The anti-tamper atomizer as set forth in claim 1, wherein the protective sleeve connecting part is fixed in the protective sleeve by interference fit;

wherein a chamfer for assisting inserting into the protective sleeve is formed on one end of protective sleeve connecting part which away from the battery cartridge connecting part;

wherein a flange is formed on an out surface of the protective sleeve connecting part, when the protective sleeve connecting part is fixed in the second end of the protective sleeve, the flange presses against an end surface on the second end of the protective sleeve so as to limit a position of the battery cartridge connector and facilitate the assembling;

wherein a male screw is formed on the battery cartridge connecting part;

wherein the anti-tamper atomizer further comprises a first insulating ring fixed in the battery cartridge connector and a first electrode fixed in the first insulating ring, wherein the first insulating ring is made of elastic material; a first retaining groove is formed on a peripheral surface of the first insulating ring, a first protrudent ring extending along a radial direction of the protective sleeve is formed in the protective sleeve connecting part, and the first retaining groove is engaged with the first protrudent ring;

wherein the suction nozzle cap comprises a cover plate with a center hole, an outer cylinder wall extending perpendicularly from the cover plate and fixed in the first end of the of the protective sleeve by interference fit, and an inner cylinder wall extending perpendicularly from the periphery of the center hole on the cover plate; and wherein oil storage cotton is in cylindric shape, with one end supported on the end of the outer cylinder wall of the suction nozzle cap and another end sleeved by the protective sleeve connecting part of the battery cartridge connector.

3. An electronic cigarette, comprising a battery cartridge and the anti-tamper atomizer and an anti-tamper atomizer connected with each other, wherein the anti-tamper atomizer comprises a protective sleeve, a suction nozzle cap fixed on a first end of the protective sleeve, and a battery cartridge connector fixed on a second end of the protective sleeve, a vent pipe, a heater strip component and an oil storage cotton coated outside of the vent pipe and the heater strip component are arranged in the protective sleeve, the battery cartridge connector comprises a protective sleeve connecting part and a battery cartridge connecting part connected with each other, wherein the battery cartridge connector has a center hole extending along the axis of the protective sleeve, and a groove formed by cutting an outer surface of the battery cartridge connector is formed at an adjacency of the protective sleeve connecting part and the battery cartridge connecting part;

wherein a peripheral surface of a cross section of battery cartridge connector at the groove in a direction perpendicular to an axis of the protective sleeve comprises multiple recesses arranged alternately, and a bulge is formed between every two adjacent recesses;

wherein the recesses are positioned uniformly on a same circumference around the axis of the protective sleeve; depths of the recesses are the same, and height of each bulge is same with each other;

wherein the battery cartridge connector has a wall thickness of 0.05 mm to 0.1 mm at the recesses and a wall thickness of 0.1 mm to 0.2 mm at the bulge; and wherein the battery cartridge connector groove is broken at the groove when a force is applied on the battery cartridge connector at a direction perpendicular to the protective sleeve to bend the battery cartridge connector.

4. The electronic cigarette as set forth in claim 3, wherein the protective sleeve connecting part is fixed in the protective sleeve by interference fit;

wherein a chamfer for assisting inserting into the protective sleeve is formed on one end of protective sleeve connecting part which away from the battery cartridge connecting part;

wherein a flange is formed on an out surface of the protective sleeve connecting part, when the protective sleeve connecting part is fixed in the second end of the protective sleeve, the flange presses against an end surface on the second end of the protective sleeve so as to limit a position of the battery cartridge connector and facilitate the assembling;

wherein a male screw is formed on the battery cartridge connecting part; and wherein the anti-tamper atomizer further comprises a first insulating ring fixed in the battery cartridge connector and a first electrode fixed in the first insulating ring, wherein the first insulating ring is made of elastic material; a first retaining groove is formed on a peripheral surface of the first insulating ring, a first protrudent ring extending along a radial direction of the protective sleeve is formed in the protective sleeve connecting part, and the first retaining groove is engaged with the first protrudent ring.

* * * * *